United States Patent
Csete et al.

(10) Patent No.: US 6,184,035 B1
(45) Date of Patent: Feb. 6, 2001

(54) METHODS FOR ISOLATION AND ACTIVATION OF, AND CONTROL OF DIFFERENTIATION FROM, SKELETAL MUSCLE STEM OR PROGENITOR CELLS

(75) Inventors: Marie Csete; John Doyle, both of South Pasadena; Barbara Wold, San Marino, all of CA (US)

(73) Assignee: California Institute of Technology, Pasadena, CA (US)

(*) Notice: Under 35 U.S.C. 154(b), the term of this patent shall be extended for 0 days.

(21) Appl. No.: 09/195,569

(22) Filed: Nov. 18, 1998

(51) Int. Cl.$^7$ .................................................. C12N 5/00
(52) U.S. Cl. ............................................ 435/377; 435/375
(58) Field of Search .................................... 435/375, 377

(56) References Cited

U.S. PATENT DOCUMENTS

| | | | |
|---|---|---|---|
| 5,328,695 | 7/1994 | Lucas et al. | 424/426 |
| 5,550,050 | 8/1996 | Holland et al. | 435/240.2 |
| 5,728,581 | 3/1998 | Schwartz et al. | 435/385 |
| 5,750,376 | 5/1998 | Weiss et al. | 435/69.52 |

OTHER PUBLICATIONS

Iyer et al. Genes and Development. Jan. 1998, vol. 12, pp. 149–162.*

Sorokan et al. Molecular Biology of the Cell. 1996. vol. 7, No. Suppl., p. 317A.*

Colton, Carol A. et al., "Protection from Oxidation Enhances the Survival of Cultured Mesencephalic Neurons," *Experimental Neurology*, 132, pp. 54–61 (1995).

Nurse, Colin A. et al., "Role of Basic FGF and Oxygen in Control of Proliferation, Survival and Neuronal Differentiation in Carotid Body Chromaffin Cells," *Developmental Biology*, 184, pp. 197–206 (1997).

Czyzyk–Krzeska, Maria F. et al., "Hypoxia Increases Rate of Transcription and Stability of Tyrosine Hydroxylase mRNA in Pheochromocytoma (PC12) Cells," *The Journal of Biological Chemistry*, vol. 269, No. 1, pp. 760–764, Jan. 7, 1994.

Brewer, G.J. et al., "Survival and Growth of Hippocampal Neurons in Defined Medium at Low Density Advantages of a Sandwich Culture Technique or Low Oxygen," *Brain Research* (Abstract).

Koller, Manfred R. et al., "Effects of Synergistic Cytokine Combinations, Low Oxygen, and Irradiated Stroma on the Expansion of Human Cord Blood Progenitors," *Blood*, vol. 80, No. 2, pp. 402–411, Jul. 15, 1992.

Potocnik, Alexandre J., "In vitro generation of lymphoid precursors from embryonic stem cells," *The EMBO Journal*, vol. 13, No. 22, pp. 5274–5283, 1994.

Kagamu, Hiroshi et al., "Low Oxygen Enhances Endothelin–1 (ET–1) Production and Responsiveness to ET–1 in Cultured Cardiac Myocytes," *Biochemical and Biophysical Research Communications*, vol. 202, No. 3, pp. 1612–1618, Aug. 15, 1994.

Studer, Lorenz et al., "Transplantation of expanded mesencephalic precursors leads to recovery in parkinsonian rats," *Nature Neuroscience*, Vo. 1, No. 4, pp. 290–295, Aug. 1998.

Genbacev, Olga et al., "Regulation of Human Placental Development by Oxygen Tension," *Science*, vol. 277, pp. 1669–1672, Sep. 12, 1997.

Ivàn J. Sosa, M.D. et al., "Isolation and Long–term Survival of Adult Human Sensory Neurons In Vitro," *Neurosurgery*, vol. 42, No. 3, Mar. 1998, pp. 681–686.

Hiromi Takahashi et al., "Effect of Chronic Hypoxia on Skeletal Muscle Fiber Type in Adult Male Rats," *Ann. Physiol. Anthrop.*, 11(6), 1992, pp. 625–630.

R. A. Metcalfe et al., "Stimulation of extraocular muscle fibroblasts by cytokines and hypoxia: possible role in thyroid–associated ophthalmopathy," *Clinical Endocrinology* 40, 1994, pp. 67–72.

Eugene D. Robin et al., "Coordinate Regulation of Glycolysis by Hypoxia in Mammalian Cells," *Journal of Cellular Physiology*, 118, 1984, pp. 287–290.

N.V. Darinskii et al., "Effect of The Conditions of Antenatal Development on Functional Maturation of Rabbit Fetal Skeletal Muscle," *Bulletin of Experimental Biology and Medicine*, vol. 77, No. 2, Feb. 1974, pp. 104–106.

Boris Kuzin et al., "Nitric Oxide Regulates Cell Proliferation during Drosophila Development," *Cell*, vol. 87, Nov. 15, 1996, pp. 639–649.

Alice P. Pentland, M.D. et al., "Modulation of Proliferation in Epidermal Keratinocyte Cultures by Lowered Oxygen Tension," *Experimental Cell Research*, 145, 1983, pp. 31–43.

Maria G. Cipolleschi et al., "The Role of Hypoxia in the Maintenance of Hematopoietic Stem Cells," *Blood*, 82(7), 1993, pp. 2031–2037.

Alice P. Pentland, M.D. et al., "Effects fo Gas Tension on Epidermal Keratinocyte DNA Synthesis and Prostaglandin Production," *The Journal of Investigative Dermatology*, vol. 86, No. 2, Feb. 1986, pp. 177–180.

Takashi Horikoshi, M.D. et al., "Effect of Oxygen on the Growth of Human Epidermal Keratinocytes," *The Journal of Investigative Dermatology*, vol. 86, No. 4, Apr. 1986, pp. 424–427.

(List continued on next page.)

*Primary Examiner*—Sandra E. Saucier
*Assistant Examiner*—Vera Afremova
(74) *Attorney, Agent, or Firm*—Brinks Hofer Gilson & Lione

(57) ABSTRACT

The present invention provides a method of isolating, maintaining, and/or enriching for stem or progenitor cells derived from diverse organ or tissue sources. The invention specifically teaches that these can be accomplished by the controlled use of subatmospheric oxygen culture, and that the precise oxygen level or levels must be determined empirically and/or by reference to physiologic levels within intact functioning organ or tissue. In particular, culturing skeletal muscle progenitor cells in less than 12% oxygen conditions or under 1% oxygen level.

16 Claims, No Drawings

OTHER PUBLICATIONS

Thomas G. Storch, "Oxygen Concentration Regulates 5–azacytidine–induced myogenesis in $C_3H/10T1/2$ cultures," *Biochimica et Biophysica Acta,* 1055, 1990, pp. 126–129.

D.D.W. Cornelison et al., "Single–Cell Analysis of Regulatory Gene Expression in Quiescent and Activated Mouse Skeletal Muscle Satellite Cells," *Developmental Biology* 191, 1997, pp. 270–283.

* cited by examiner

US 6,184,035 B1

METHODS FOR ISOLATION AND ACTIVATION OF, AND CONTROL OF DIFFERENTIATION FROM, SKELETAL MUSCLE STEM OR PROGENITOR CELLS

FEDERALLY SPONSORED RESEARCH OR DEVELOPMENT

The U.S. Government has certain rights in this invention pursuant to Grant Nos. NIH-5T32GM07616 and AR40780, AR42671, and AG14435 awarded by the National Institutes of Health, and DARPA/AFOSR grant number F49620-98-1-0487 granted by the Air Force Office of Scientific Research.

BACKGROUND OF THE INVENTION

Regeneration after injury in post-natal organ systems, in many ways, recapitulates developmental processes during embryogenesis. Though many interesting and crucial individual genes that are important for embryogenesis and organogenesis have been discovered over the past decade, the integrated regulation of the process is in many ways unknown (Barinaga, 1994), as are the similarities and differences between embryonic development and regeneration/ healing of post-natal cells, tissues and organs. In embryonic mice and man, the various tissue systems develop in parallel and use both inter- and intra-tissue signaling, while the environment around the tissue progresses from one dependent on diffusion of oxygen to one in which oxygen is supplied via the developing vascular system. In the embryo over time, oxygenation to tissues increases as the blood supply is laid down and extended, but this delivery of oxygen is not homogenous throughout any tissue. And though oxygenation becomes richer as the embryo grows, levels of oxygen present in the embryo are generally considered insufficient for normal adult tissue functioning.

Each tissue and organ develops by an exquisitely organized progression in which relatively unspecialized or "undifferentiated" progenitor or stem cells give rise to progeny that ultimately assume distinctive, differentiated identities and functions. Mature tissues and organs are composed of many types of differentiated cells, with each cell type expressing a particular subset of genes that in turn specifies that cell's distinctive structure, specialized function, and capacity to interact with and respond to environmental signals and nutrients. These molecular, structural and functional capacities and properties comprise the cell phenotype. A similar course of coupled cell proliferation and differentiation in the presence of changing local $O_2$ supply occurs when an injured or degenerating adult tissue undergoes repair and regeneration. The level of oxygen is especially pertinent in many regeneration paradigms in which normal blood supply is reduced or even transiently stopped by trauma or embolic events (myocardial infarction, stroke).

The hypothesis that $O_2$ levels have significant differential impact on different cell types or states has so far received little explicit attention in the literature, with the exception of formation of the vasculature itself. In particular it is important to note that the vast preponderance of studies of regeneration in vitro are performed in laboratories using room air oxygen levels. In room air, 20–21% of atmospheric gas is oxygen (at sea level depending on humidity), which translates into an oxygen partial pressure of 160 mm Hg [0.21(760 mm Hg)]. The most highly oxygenated tissue in the human body is the arterial blood supply with an oxygen partial pressure of 90 mm Hg. Normal venous oxygenation is 40 mm Hg, and mean tissue oxygen level is 26 mm Hg. However, the vast majority of regeneration research or research on the culture of progenitor cells, stem cells, or differentiating products ignores the importance of oxygenation: The average tissue culture condition is 21% oxygen and 5% carbon dioxide which the remainder being nitrogen.

Herein, the inventors demonstrate that regulated oxygen levels, particularly subatmospheric levels of oxygen (i.e. levels below 21% oxygen and 5% carbon dioxide), can be used to exploit responses of stem and progenitor cells that differ from the response of other cells as a simple and general pathway for their isolation, maintenance, proliferation, enrichment, and/or selective developmental progression and differentiation. This work has important implications for clinical tissue and organ transplantation.

In a time of critical shortages of donor organs, efforts to bring cellular transplantation into the clinical arena are urgently needed (Neelakanta & Csete, 1996). For example, in the case of the liver, a stem cell has not been rigorously identified, and animal models of transplantation of fully-differentiated liver cells (normally quiescent and difficult to force into division experimentally) are not yet successful enough to warrant clinical trials. However, a liver stem cell would represent the ideal cellular transplant because of the potential to regenerate substantial organ function from a tiny rudiment. Thus, there remains a need for methods to identify cells (progenitors and stems) which can be used to regenerate tissue. The present invention is directed at these goals.

BRIEF SUMMARY OF THE INVENTION

The present invention provides a method of isolating, maintaining, and/or enriching for stem or progenitor cells derived from diverse organ or tissue sources. The method can also be used to influence specific differentiation pathways, to alter the kinetics of developmental progression or differentiation or to alter the yield of one cell phenotype over other possible types via the use of subatmospheric or sub-physiologic oxygen levels. The invention specifically teaches that these can be accomplished by the controlled use of subatmospheric oxygen culture, and that the precise oxygen level or levels must be determined empirically and/or by reference to physiologic levels within intact functioning organ or tissue, or that tissue following injury, regeneration, or disease.

The inventors have discovered that when adult skeletal muscle fibers are cultured under physiologically hypoxic conditions, progenitor cells (which represent a source of regenerated new muscle) develop in greater numbers than when fibers are grown under traditional room air conditions. Furthermore, this subatmospheric oxygen-induced enrichment of the skeletal muscle progenitor population is followed by earlier regeneration of new skeletal muscle in culture.

Intentional hypoxia has been used in some culture systems, usually differentiated systems, to mimic pathologic conditions such as stroke (for example, Papadopoulos et al., 1996). In some circumstances, whole embryos have been cultured under subatmospheric oxygen conditions to mimic gestation (for example, Giles & Foote, 1997). In other circumstances reduced oxygen conditions are used as part of a broad range of tests of many environmental parameters on culture integrity (for example, Berthelot & Terqui, 1996). In a few cases oxygen conditions have been used to assess proliferation of particular cells as a function of oxygen levels (for example, Matsuda et al., 1998). However, such examples do not teach the general principle that an intentional reduction of oxygen surrounding cultures can be used to selectively promote survival, proliferation, enrichment or particular developmental or differentiation pathways from stem cell and/or progenitor cells. Furthermore, such reports have not had an effect on the general state or practice of the art, in that almost all tissue culture continues to be conducted in room air.

DETAILED DESCRIPTION OF THE INVENTION

A method for isolating, maintaining, propagating or enriching progenitor or stem cells, and/or for influencing the differentiation outcome or differentiation kinetics of such cells into particular tissue types, comprising the steps of:
  a) obtaining cells derived from mammalian tissue containing at least one progenitor cell or stem cell capable of producing progeny that can assume or produce cells with one or more differentiated phenotypes, and
  b) culturing the cells derived from such mammalian tissue (various organ and tissue types) in suitable medium under empirically determined subatmospheric oxygen conditions for a time sufficient to promote the survival, proliferation, or enrichment of the stem or progenitor population, or to cause or influence entry into one or more differentiation pathways.

Definitions

A "stem cell" is a relatively undifferentiated cell that can be induced to proliferate and that can produce progeny that subsequently differentiate into one or more mature cell types, while also retaining one or more cells with parental developmental potential. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype.

"Progenitor cells" have a cellular phenotype that is more primitive (i.e., is at an earlier step along a developmental pathway or progression than is a fully differentiated cell). Often, progenitor cells also have significant or very high proliferative potential. Progenitor cells may give rise to multiple distinct differentiated cell types or to a single differentiated cell type, depending on the developmental pathway and on the environment in which the cells develop and differentiate. Like stem cells, it is possible that cells that begin as progenitor cells might proceed toward a differentiated phenotype, but then "reverse" and re-express the progenitor cell phenotype.

"Differentiation" refers to the developmental process whereby cells assume a specialized phenotype, i.e., acquire one or more characteristics or functions distinct from other cell types. In most uses, the differentiated phenotype refers to a cell phenotype that is at the mature endpoint in some developmental pathway. In many but not all tissues, the process of differentiation is coupled with exit from the cell cycle—in these cases, the cells lose or greatly restrict their capacity to proliferate when they differentiate.

"Subatmospheric" conditions mean any oxygen concentration below about 20%, preferably below about 12%, more preferably below about 8%, at sea level.

"Physiologic" oxygen levels are the range of oxygen levels normally found in healthy tissues and organs. These levels vary depending on tissue type.

"Hypoxia" occurs when the normal physiologic levels of oxygen are not supplied to a cell or tissue. "Normoxia" refers to normal physiologic levels of oxygen for the particular cell type, cell state or tissue in question. "Anoxia" is the absence of oxygen. "Hypoxic conditions" are those leading to cellular hypoxia. These conditions depend on cell type, and on the specific architecture or position of a cell within a tissue or organ, as well as the metabolic status of the cell. A critical point is that in most cell biology research of the past 25 years, ambient atmospheric oxygen levels of 20–21% are routinely called and experimentally taken to be "normoxic," but this assumption is physiologically erroneous. In this historic context, much cell culture literature refers to any condition with oxygen lower than ambient atmospheric as "hypoxic," but this usage is also physiologically incorrect.

"Acidosis" means that the pH is below normal physiologic levels.

"Enriching" of cells means that the yield (fraction) of cells of one type is increased over the fraction of cells of that type in the starting culture or preparation.

"Proliferation" refers to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

"Regeneration" means regrowth of a cell population, organ or tissue after disease or trauma.

Methods for manipulating the yield of progenitor/stem cell cultures or preparations by manipulation of sub-atmospheric oxygen levels The present invention provides a method for manipulating the yield of progenitor/stem cell cultures. This method has several embodiments, including:
  A. Subatmospheric/physiologic oxygen conditions used to culture or enrich stem cell and/or progenitor cells
  B. Subatmospheric/physiologic oxygen conditions used to isolate/identify stem or progenitor cells that are not yet identified
  C. Subatmospheric/physiologic oxygen conditions used to alter the kinetics of developmental progression or accelerate differentiation from stem cell and/or progenitor populations
  D. Subatmospheric/physiologic oxygen conditions used to enhance regeneration
  E. Subatmospheric/physiologic oxygen conditions used to select, promote or reinforce a specific cell fate or fates A. Subatmospheric/physiologic oxygen conditions used to culture or enrich stem cells and/or progenitor cells A method of enriching progenitor or stem cells in a population of cells comprising progenitors or stems, progeny thereof, and other "contaminating" cells, comprising the steps of:
  a) obtaining a population of mammalian cells (adult or embryonic; from one or more solid tissue type) containing at least one stem cell or progenitor cell capable of producing differentiated progeny, and b) culturing the cells derived from mammalian tissue in suitable medium under oxygen levels reflecting physiologic oxygenation for the tissue from which they were derived or under hypoxic conditions (below normal physiologic oxygenation) for a time sufficient to enrich the population of progenitor/stem cells in said culture relative to one or more other cell types in the population.

The low oxygen or physiologic oxygen conditions are part of the enrichment process from either the time of isolation or some time after (such as after attachment of cells to tissue culture plates) or throughout the process, depending on the specific cell type to be enriched and depending on the particular starting cell population and its physiologic status. Enrichment of stems/progenitors by physiologic or low levels of oxygen may be the result of one or more mechanisms that include (1) increase in the absolute number of stem cell and/or progenitor cells (2) enrichment by selective survival of progenitor/stem cells, or (3) enrichment of stems/progenitors by their selective proliferation.

Any increase in the number of stems/progenitors is significant in that more cells are then available to regenerate a greater volume of new tissue. Any enrichment, even without increase in number, is important in applications where limitations on total cell number are pertinent or when the effects of the non-stem/non-progenitor contaminants are negative for the desired outcome or for defining the material adequately. Any enhancement of survival of the stem or progenitor state, even without increase in stem cell and/or progenitor cell number or any enrichment of stem cell and/or progenitor cell types is valuable in settings where culture is required (i.e., to handle tissue before administration of cell therapy, or to permit any other procedure during which the cells must survive such as transfection of genes, drug treatment, or enrichment by cell sorting or other additional procedures).

Suitable solid tissue from which cells can be obtained includes any organ or tissue from adult, post-natal, fetal or embryonic mammalian tissue. Any mammalian tissue or organ can be used in this invention, including but not limited to those obtained from mice, cattle, sheep, goat, pigs, dogs, rats, rabbits, and primates (including human). Specific examples of suitable solid tissues include skeletal muscle, brain and central nervous system tissue from which neurons and other supporting cells are derived, skin derived from cultured keratinocytes, germ cells or embryonic stem cells or cells from other organs (liver, pancreas, spleen, kidney, thyroid, etc.). Stem cells and progenitor cells isolated from any other solid organ are also amenable candidates for culturing under physiologic or hypoxic conditions.

Suitable medium and conditions for generating primary cultures are well known in the art and vary depending on cell type. For example, skeletal muscle, bone, neurons, skin, liver, and embryonic stem cells are all grown in media differing in their specific contents. Furthermore, media for one cell type may differ significantly from lab to lab and institution to institution. As a general principle, when the goal of culturing is to keep cells dividing, serum is added to the medium in relatively large quantities (10–20% by volume). Specific purified growth factors or cocktails of multiple growth factors can also be added or sometimes used in lieu of serum. As a general principle, when the goal of culturing is to reinforce differentiation, serum with its mitogens is generally limited (about 1–2% by volume). Specific factors or hormones that promote differentiation and/or promote cell cycle arrest can also be used.

Physiologic oxygen and hypoxic oxygen conditions can be used at any time during the growth and differentiation of cells in culture, as a critical adjunct to selection of specific cell phenotypes, growth and proliferation of specific cell types, or differentiation of specific cell types. In general, physiologic or hypoxic oxygen-level culturing is accompanied by methods that limit acidosis of the cultures, such as addition of strong buffer to medium (such as Hepes), and frequent medium changes.

Cells can be exposed to hypoxic/physiologic conditions using a variety of means. Specialized laboratory facilities may have completely enclosed environments in which the oxygen levels are controlled throughout a dedicated, isolated room. In such specialized areas, low oxygen levels can be maintained throughout the isolation, growth and differentiation of cells without interruption. Very few laboratories have such specialized areas. Physiologic or low oxygen culturing conditions can be maintained by using commercially-available chambers which are flushed with a pre-determined gas mixture (Billups-Rothenberg, San Diego Calif.). As an adjunct, medium can be flushed with the same gas mixture prior to cell feeding. In general, it is not possible to maintain physiologic or hypoxic oxygen conditions during cell feeding and passaging using these smaller enclosed units, and so, the time for these manipulations should be minimized as much as possible. Any sealed unit can be used for physiologic oxygen or hypoxic culturing provided that adequate humidification, temperature, and carbon dioxide are provided.

Physiologic oxygen conditions range widely depending on the cell type, energy expenditure, and location within an organ structure. Physiologic conditions range from about 12% at the high extreme to less than 1% oxygen, but preferably in the range of 1–5% (about 8–40 mm Hg). (Guyton & Hall, 1996). Hypoxic conditions are generally less than 1% oxygen, but some cells may be hypoxic at 1% oxygen or higher.

In addition to oxygen, the other gases for culture are typically 5% carbon dioxide and the remainder is nitrogen, but optionally may contain varying amounts of nitric oxide (starting as low as 3 ppm), carbon monoxide and other gases, both inert and biologically active. Carbon dioxide concentrations typically range around 5% as noted above, but may vary between 2–10%. Both nitric oxide and carbon monoxide are typically administered in very small amounts (i.e. in the ppm range), determined empirically or from the literature.

The optimal physiologic or hypoxic conditions for any given progenitor/stem cell type will vary. A skilled artisan could determine suitable subatmospheric conditions by generating an oxygen dose response curve, in which carbon dioxide is kept constant, and oxygen levels are varied (with nitrogen as the remaining gas). For example, to determine the optimal ambient oxygen culturing conditions for expansion of a stem cell and/or progenitor, one would establish cultures from an organ system. The initial culture is mixed, consisting of some differentiated cells, cells of other developmental lineages or pathways, as well as stem cell and/or progenitor cells. After exposure to the various oxygen levels (e.g. 1%, 2%, 5%, 10% and 15%), the number and function of stem cell and/or progenitor cells is assessed by methods appropriate to the system. In some cases, a constellation of molecular markers is available to rapidly identify the stem cell population. But in other cases, a single marker coupled with proliferation assays is appropriate, while in other cases proliferation assays alone are appropriate. In some cases all or some of the above assays are coupled with bioassays to follow the differentiation potential of the presumed stem cells. Overall, the precise assays used to determine stem cell and/or progenitor response to oxygen levels are dependent on the nature of the system examined as well as available markers and techniques specific to that system.

The timing of physiologic or low oxygen conditions is also part of the oxygen dose response curve. Some cells may be more or less sensitive to oxygen immediately after isolation while some cells may respond only after some time in culture. The timing of physiologic or low oxygen conditions absolutely and in relation to other manipulations of the cultures is part of assessing the optimal oxygen culturing conditions. Furthermore, the mitogenic effects of other gases may be synergistic with physiologic or low oxygen conditions. Different gene regulatory networks may be induced by low/physiologic oxygen culturing during different phases of culture. During expansion of stems/progenitors, low oxygen may induce gene expression distinct from that induced by low oxygen during differentiation.

The cells are typically exposed to hypoxic conditions for a time sufficient to enrich the population of progenitor/stem cells compared to other cell types. Typically this is for 1 or more hours, preferably 3 or more hours, more preferably 6 or more hours, and most preferably 12 or more hours, and may be continuous. The temperature during the culture is typically reflective of core body temperature, or 37° C., but may vary between 32 and 40° C.

Following an initial exposure to low or physiologic oxygen culturing conditions, cells can be maintained in these conditions or returned to normal laboratory oxygen conditions, depending on the desired outcome. Stem cell and/or progenitors may be maintained continuously in low or physiologic oxygen culture conditions.

It is understood that the initial medium for isolating stems/progenitors, the medium for proliferation of these cells, and the medium for differentiation of these cells can be the same or different. All can be used in conjunction with low or physiologic oxygen level culturing. The medium can be supplemented with a variety of growth factors, cytokines, serum, etc. Examples of suitable growth factors are basic fibroblast growth factor (bFGF), vascular endothelial growth factor (VEGF), epidermal growth factor (EGF), transforming growth factors (TGFα and TGFβ), platelet derived growth factors (PDGF's), hepatocyte growth factor (HGF), insulin-like growth factor (IGF), insulin, erythropoietin (EPO), and colony stimulating factor (CSF). Examples of suitable hormone medium additives are estrogen, progesterone or glucocorticoids such as dexamethasone. Examples of cytokine medium additives are interferons, interleukins, or tumor necrosis factor-α (TNFα). One skilled in the art will test additives and culture components at varied oxygen levels, as the oxygen level may alter cell response to, active lifetime of additives or other features affecting their bioactivity.

Stem cells and progenitor cells isolated from solid tissues (the exception to solid tissue is whole blood, including blood, plasma and bone marrow) which were previously unidentified in the literature are also within the scope of this invention.

B. Subatmospheric/physiologic oxygen conditions used to isolate/identify stem or progenitor cells that are not yet identified In this embodiment, a culture derived from an organ or tissue system is established, consisting of a variety of cell types, both stem cell and/or progenitor and differentiated cells. Oxygen dose-response experiments are performed, in which parallel cultures are exposed to progressively decreasing levels of oxygen, starting with 12% (approximately adult arterial levels). The goal of these experiments is to identify the oxygen level at which stem cell and/or progenitor cells increase in absolute number, or survive in preference to other cells in the culture, or selectively proliferate, or a combination of these effects. In any of these cases, subatmospheric oxygen is used to facilitate identification and characterization of the usually rare stem cell and/or progenitor cell population.

Following culturing in physiologic or low oxygen conditions, progenitor/stem cells can be identified by a variety of methods. Progenitor/stem cells with defined morphology can often be identified visually, but their precise identification is made with specific markers such as antibodies, or by their expression of specific genes at the mRNA level (using PCR). Following culturing in physiologic or low oxygen conditions, one can determine if stems/progenitors are proliferating by a variety of means including incorporation of radionucleotides (such as $^3$H-thymidine), or by uptake of BrdU (a thymidine analog) (Assy & Minuk, 1997). Some progenitor/stem cells will be identified by their ability to differentiate into specific cell types, and this assay may be used alone or in combination with other assays as above, depending on the availability of suitable markers.

C. Subatmospheric/physiologic oxygen conditions used to alter the kinetics of developmental progression or accelerate differentiation from stem cell and/or progenitor populations Another embodiment of the present invention involves sifting the kinetics or the yield of differentiation of progenitor cells and/or stem cells into various cell types by exposing them to physiologic/subatmospheric oxygen levels. In this embodiment, subatmospheric oxygen is used to alter the kinetics of progression from an undifferentiated stem cell and/or progenitor state to cells with a differentiated phenotype. This change in kinetics, depending on the cell type and culture conditions may be an acceleration or deceleration. Moreover, the use subatmospheric oxygen may increase or decrease the fraction of stem cells or progenitor cells that differentiate. Depending on the application, such increase or decrease might be desirable.

The steps involved in this embodiment are identical to those described above for enriching the population of stem cells. However, the conditions may differ as to absolute timing of physiologic/subatmospheric oxygen added to the culture, and timing of physiologic/subatmospheric oxygen culturing relative to other culture manipulations. Differentiation medium is generally different than medium supplemented to encourage growth and proliferation. In general, differentiation medium is low in mitogens from serum additives.

In some stem cell and/or progenitor cultures, physiologic/subatmospheric oxygen conditions dramatically increase the rate of differentiation in culture. The inventors have shown, for example, that when rat embryonic brain stem cells are placed in 1% oxygen cultures (for 7–10 days), more differentiated neurons, astrocytes, and oligodendrocytes are produced per plated stem cell than under normal laboratory oxygen conditions. This is an example of kinetic enhancement of differentiation which is also applicable to other systems. For example, the inventors have also shown an increase in kinetics of progression and initiation of differentiation in skeletal muscle progenitor cells.

Following differentiation, the specific differentiated cell types are identified by a variety of means including fluorescence activated cell sorting (FACS), protein-conjugated magnetic bead separation, morphologic criteria, specific gene expression patterns (using RT-PCR), or specific antibody staining. The gene products expressed between two or more given differentiated cell types will vary. For example, following differentiation of skeletal muscle satellite cells, the transcription factors myf5, MyoD, myogenin, and mrf4 are expressed. It is understood that developmental pathways often involve more than one step or stage for differentiation and any of these steps or stages may be affected by subatmospheric oxygen.

D. Subatmospheric/physiologic oxygen conditions used to enhance regeneration

In this embodiment, subatmospheric oxygen is used to first expand the stem cell and/or progenitor pool, from which regeneration is then allowed to proceed. Since the initial pool from which tissue/organ can be regenerated is increased in number, the ultimate amount of regeneration into differentiated cells is also increased.

In skeletal muscle primary cultures, the inventors showed that the number of progenitor satellite cells on parental fibers increases twice as fast in culture for the first 60 hours when the fibers are cultured under 1% oxygen versus the normal room air oxygen levels. This is an example of more tissue generated for differentiation by hypoxic culturing conditions.

E. Subatmospheric/physiologic oxygen conditions used to select, promote or reinforce or promote a specific cell fate or fates When a particular stem or progenitor cell is capable of differentiating into a number of developmentally distinct cell, tissue, or organ types, the cell is said to be pluripotent. By incubating a pluripotent cell line under hypoxic conditions in vitro, the inventors were able to manipulate or skew the direction of differentiation of the cell population.

The result of this technique is essentially an enrichment of one or more cell type but this may also be considered a selection against other cell types. In this example, growth of the cells under hypoxic conditions enriched for muscle cells and, at the same time, selected against fat cells. The inventors contemplate that oxygen concentrations may be manipulated to direct differentiation of other pluripotent stem or progenitor cells as well.

Specifically, the mouse cell line 10T1/2 cells can be pharmacologically (5-azacytidine) induced to generate cartilage, skeletal muscle and fat (adipocytes) (Taylor & Jones, 1979). Previous work subjecting these cells to 2% oxygen suggested that the numbers of skeletal muscle cells generated was increased by low oxygen conditions (Storch TG, 1996). The present inventors have shown that culturing of 10T1/2 cells under 21% oxygen conditions in conjunction with 5-azacytidine treatment results in skeletal muscle and adipocyte differentiation within 2 weeks. Notably, adipocyte differentiation in this cell line is blocked under 1% oxygen conditions in the presence (or absence) of azacytidine. This is an example of physiologic/subatmospheric oxygen conditions playing a role in the precise differentiation fate taken by pluripotent cells. The identification of gene networks up- or down-regulated by the change in oxygen environment could, in turn, provide pharmacologic targets for enhancement or blocking of specific differentiation pathways, in this case fat development.

In this embodiment, subatmospheric oxygen conditions can be used to exploit expression of particular genes characteristic of certain differentiated cell types. For example, the inventors have shown that culture of embryonic rat brain stem cells in 1% oxygen (vs. 20–21%) leads to increased expression of the gene tyrosine hydroxylase after 10 days in culture, when neuronal differentiation has occurred. Tyrosine hydroxylase is the rate-limiting enzyme in the synthetic pathway to dopamine. Deficiency of dopamine in certain areas of the brain is the cause of Parkinson's disease. Thus culturing, expansion, and differentiation of central nervous system stem cells under low $O_2$ may be used to maximize the efficiency of production of a therapeutic gene by differentiated progeny of the cultured cells (i.e. specific genes are regulated by low $O_2$ conditions or specific gene products are expressed by specific differentiated progeny). Techniques for screening the effect of various pharmacological agents on differentiation and/or regeneration To determine whether a test compound modulates cell proliferation and/or differentiation, a cell is identified as a progenitor cell (e.g., by using one of the above-described methods), the progenitor cell (typically a culture of progenitor cells) is contacted with the test compound, and the progenitor cell is monitored to assess the effect, if any, of the test compound on proliferation, differentiation and/or regeneration. Any compound of interest can be used as the test compound in this method.

The compound can be contacted with the progenitor/stem cells at any desired concentration, preferably, a wide range of concentrations. The cells are monitored for changes in the rates or patterns of proliferation and/or differentiation of the progenitor cell in order to determine which test compounds modulate proliferation and/or differentiation. Typically, such assays are performed in vitro.

Stem cell and/or progenitor cells subjected to physiologic/subatmospheric oxygen conditions will express different genes than those cultured under routine conditions. It is well known, for example, that physiologic hypoxia elicits expression of HIF-1 (hypoxia inducible factor-1) in a variety of tissues (Iyer et al., 1998). This gene, in turn, causes increased expression of an array of other genes required for the cells to respond to hypoxia, such as erythropoietin and VEGF. Other genes have increased expression under hypoxic conditions, apparently independent of HIF-1. These genes include tyrosine hydroxylase (Ramsey et al., 1996), which is the rate limiting enzyme in the pathway to dopamine synthesis.

The kinetic differences in stem cell and/or progenitor proliferation demonstrated by the inventors, and the differences in type of differentiation in some cells shown by the inventors, are all clear indications that other genetic regulatory networks are dramatically changed by physiologic/subatmospheric culture conditions.

Methods for determining the biochemical effect of hypoxia

In light of the present disclosure, one of skill in the art would understand that the ability to isolate, culture, and differentiate progenitor cells allows for the analysis or discovery of genes that contribute to the phenotype of the progenitor cell and cells differentiated therefrom. The ability to detect genes that are differentially expressed in two cell types or populations combined with advances of rapid gene detection and sequencing technologies has led to the discovery of many novel genes that contribute to the difference in the cell types or populations. Such technologies may be used to compare gene expression in cells cultured under varying oxygen concentrations, in progenitor cells of different origin, between cells of distinct differentiation states, and in cells contacted with a compound or environmental stimulus that may affect the ability of the cells to react to a variation in oxygen concentration.

Methods of differential display have been used to elucidate the genes responsible for a difference in phenotypes between two relatively similar cell types or during sequential changes of a cell from one state to another. For example, using the differential display technique, Kocher et al. (1995) selected for genes that were up-regulated in renal cell carcinoma compared with normal renal parenchyma. Through this method, Kocher et al. (1995) were able to isolate a gene (DD96) that was rarely expressed in normal epithelial cell populations, expressed diffusely in malignant epithelial cells of the wide majority of carcinomas, and markedly overexpressed in carcinomas originating from the colon, breast, and lung. A similar technique may be used to compare gene expression in cells incubated under normal or hypoxic conditions. Genes up-regulated in one population over the other then may be used as a probe to screen for expression of that gene in other cell populations or the same cell population under different culturing conditions (i.e., in the presence of compounds or environmental stimuli that may affect the expression of the gene).

Kang et al. (1998) have developed a reciprocal subtraction differential RNA display (RSDD) method that permits the rapid and efficient identification and cloning of both abundant and rare differentially expressed genes. The technology was used to analyze gene expression alterations resulting during cancer progression as adenovirus-transformed rodent cells developed an aggressive transformed state (Kang et al., 1998). The approach resulted in the identification and cloning of known and unknown sequences that displayed expression as a function of progression and suppressed expression as a function of progression (Kang et al., 1998). The RSDD technique may be used to compare gene expression between cells during maintenance, proliferation and/or differentiation of the cells from progenitor or stem cells to fully differentiated cells in room air versus subatmospheric conditions.

The methods of differential display may be used in conjunction with rapid DNA sequencing and detection methods, allowing for the ability to screen for or sequence a large number of genes in a relatively short amount of time. U.S. Pat. No. 5,800,992 provides methods for detecting the differential expression of a plurality of genes between two cell types using complimentary polynucleotides in an array. Such technology is commonly referred to as "DNA chip" technology because the polynucleotides are deposited on a substrate that resemble computer microprocessor chips. Also described are methods of sequencing genes using DNA chips.

U.S. Pat. No. 5,834,181 utilizes similar technology to detect minor alterations in genes such as single nucleotide substitution, allowing detection of mutations in genes that lead to a change in the phenotype of a cell. Such methods may be used to determine if the inability of cells from some individual patients or animals or in cells carrying somatic mutations such as tumors to react to oxygen is caused by a mutation in one or more genes involved in oxygen-mediated/altered cell processes. In one embodiment of the present invention, cells that have an altered ability to react to oxygen concentration are analyzed using the methods of U.S. Pat. No. 5,834,181. In another embodiment of the present invention, cell cultures exposed to various levels of oxygen are analyzed using the methods of U.S. Pat. No. 5,834,181.

Methods for cellular transplant therapies

Stem cell and/or progenitors isolated, expanded, or activated by physiologic/subatmospheric oxygen culturing conditions may be used in cell/organ replacement therapies. Currently in clinical practice, pancreatic islet transplants are the only common cell transplant therapy for solid organs. In this case, pancreatic islets (differentiated cells) cultured from cadaveric donors, are transplanted to replace diseased islets, usually in patients with end-stage diabetes.

For other organs, major surgical transplant procedures are the only other real option to replace damaged or diseased organs. In theory, cellular transplant therapies could be used to replace many of these high-risk surgical procedures. But cell transplants are limited by an insufficient identification of cell populations, and insufficient supply of stems/progenitors for the various organ systems. Once a sufficient supply of stems/progenitors could be generated (either from autologous or allogeneic sources) they could, in theory, be used to regenerate a sufficient volume of cells to replace a key missing organ/tissue function(s). The regeneration could be carried out in part in the laboratory prior to transplantation of the cells and regenerated organ, or after transplantation of the cells into an orthotopic or heterotopic location in the body. The major impediment to such therapies is the availability of suitable stems/progenitors that generate sufficient tissue to perform physiologic function and withstand immune attack. The inventors propose that physiologic/subatmospheric culturing conditions can be used to identify specific populations of stem cell and/or progenitors useful for transplantation, and to expand the number of available stems/progenitors derived from a variety of culture systems.

Methods for gene therapy

Optionally, the progenitor cells obtained using the method of the present invention can be manipulated to express desired gene products. Gene therapy can be used to either modify a cell to replace a gene product, to facilitate regeneration of tissue, to treat disease, or to improve survival of the cells following implantation into a patient (i.e. prevent rejection).

In this embodiment, the progenitor cells are transfected prior to expansion and differentiation. Techniques for transfecting cells are known in the art.

A skilled artisan could envision a multitude of genes which would convey beneficial properties to the transfected cell or, more indirectly, to the recipient patient/animal. The added gene may ultimately remain in the recipient cell and all its progeny, or may only remain transiently, depending on the embodiment. For example, genes encoding angiogenic factors could be transfected into progenitor cells isolated from smooth muscle. Such genes would be useful for inducing collateral blood vessel formation as the smooth muscle tissue is regenerated. It some situations, it may be desirable to transfect the cell with more than one gene.

In some instances, it is desirable to have the gene product secreted. In such cases, the gene product preferably contains a secretory signal sequence that facilitates secretion of the protein. For example, if the desired gene product is an angiogenic protein, a skilled artisan could either select an angiogenic protein with a native signal sequence, e.g. VEGF, or can modify the gene product to contain such a sequence using routine genetic manipulation (See Nabel et al., 1993).

The desired gene can be transfected into the cell using a variety of techniques. Preferably, the gene is transfected into the cell using an expression vector. Suitable expression vectors include plasmid vectors (such as those available from Stratagene, Madison Wis.), viral vectors (such as replication defective retroviral vectors, herpes virus, adenovirus, adeno-virus associated virus, and lentivirus), and non-viral vectors (such as liposomes or receptor ligands).

The desired gene is usually operably linked to its own promoter or to a foreign promoter which, in either case, mediates transcription of the gene product. Promoters are chosen based on their ability to drive expression in restricted or in general tissue types, or on the level of expression they promote, or how they respond to added chemicals, drugs or hormones. Other genetic regulatory sequences that alter expression of a gene may be co-transfected. In some embodiments, the host cell DNA may provide the promoter and/or additional regulatory sequences.

Other elements that can enhance expression can also be included such as an enhancer or a system that results in high levels of expression.

Methods of targeting genes in mammalian cells are well known to those of skill in the art (U.S. Pat. Nos. 5,830,698; 5,789,215; 5,721,367 and 5,612,205). By "targeting genes" it is meant that the entire or a portion of a gene residing in the chromosome of a cell is replaced by a heterologous nucleotide fragment. The fragment may contain primary the targeted gene sequence with specific mutations to the gene or may contain a second gene. The second gene may be operably linked to a promoter or may be dependent for transcription on a promoter contained within the genome of the cell. In a preferred embodiment, the second gene confers resistance to a compound that is toxic to cells lacking the gene. Such genes are typically referred to as antibiotic-resistance genes. Cells containing the gene may then be selected for by culturing the cells in the presence of the toxic compound.

Methods of gene targeting in mammals are commonly used in the product of transgenic "knockout" mice (U.S. Pat. No. 5,616,491; U.S. Pat. No. 5,614,396). These techniques take advantage of the ability of mouse embryonic stem cells to promote homologous recombination, an event that is rare in differentiated mammalian cells. Recent advances in human embryonic stem cell culture may provide a needed component to applying the technology to human systems (Thomson; 1998). Furthermore, the methods of the present invention may used to isolate and enrich for stem cells or progenitors cells that are capable of homologous recombination and, therefore, subject to gene targeting technology. Indeed, the ability to isolate and grow somatic stem cells and progenitor cells has been viewed as impeding progress in human gene targeting (Yanez & Porter, 1998).

REFERRED EMBODIMENTS

Skeletal Muscle

In adult skeletal muscle, the progenitor cell is referred to as a satellite cell. Normally, satellite cells are dormant, but when muscle is traumatized, these cells divide and differentiate, and so are the source of regenerated skeletal muscle. As disclosed herein, subatmospheric oxygen culture conditions (1% oxygen) significantly increase the number of dividing satellite cells associated with myofibers over the first few days of culture. Using BrdU labeling and morphologic criteria, the number of satellites per unit length of muscle were quantified in 12 hour intervals. (The unit length of fiber was a 20× power diameter microscope field.) At each interval for the first few days, the number of satellites dividing under hypoxic conditions was about twice that under traditional room air cultures:

| | mean # BrdU positive sateliites/unit length (mean ± S.E.) | |
|---|---|---|
| Hours of assay | 21% oxygen | 1% oxygen |
| 0–12 | 0 | rare |
| 12–24 | 0.7 ± 0.1 | 1.6 ± 0.2 |
| 24–36 | 0.7 ± 0.2 | 2.1 ± 0.4 |
| 36–48 | 3.7 ± 0.6 | 5.6 ± 0.9 |
| 48–60 | 2.5 ± 0.5 | 6.3 ± 1.0 |

Methods of isolating, identifying, culturing and differentiating satellite cells are well known to those of skill in the art. For example, in U.S. Pat. No. 5,328,695, Lucas et al. describe a myogenic protein isolate from mammalian bone that stimulates lineage commitment and differentiation of skeletal muscle stem cells. Primary cultures of muscle progenitor cells were obtained from chicken embryos, cultured and caused to differentiate in vitro. The inventors contemplate that the hypoxic culturing conditions they describe herein, used in conjunction with the methods of U.S. Pat. No. 5,328,695, will further increase the isolation, activation, and differentiation of such stem cells as well as satellites derived from mammalian systems.

Cornelison and Wold (1997) isolated satellite cells from adult murine skeletal muscle and characterized the expression of certain genes in quiescent and activated satellite cells. Traditionally, quiescent satellite cells have been hard to distinguish from contaminating fibroblasts because there were no known molecular markers that could be used to distinguish the two. Using a single-cell reverse transcriptase-polymerase chain reaction (RT-PCR) technique, Cornelison and Wold (1997) demonstrated that c-met is expressed in quiescent satellite cells but not in muscle-derived fibroblasts or other mononucleated cells from healthy muscle explants. Furthermore, c-met was expressed throughout activation, proliferation, and differentiation of satellite cells. Therefore, c-met may be used as a molecular marker to detect satellite cells and cells differentiated therefrom (Cornelison & Wold, 1997).

Using the single-cell RT-PCR technique, Cornelison and Wold (1997) went on to show that, upon activation, the satellite cells showed a distinct progression of MyoD family regulators of muscle determination and differentiation (mrf's) gene expression. Activated satellite cells began to express either c-met and MyoD or c-met and myf5 first among the mrf's (Cornelison & Wold, 1997). Most cells then expressed c-met and both myf5 and MyoD simultaneously (Cornelison & Wold, 1997). This state was followed by one in which the cells expressed c-met, myf5, MyoD, and myogenin (Cornelison & Wold, 1997). Although rare cells later expressed c-met and myogenin, others expressed all the MRFs of the previous state plus MRF4 (Cornelison & Wold, 1997). In the next state, myf5 and MyoD expression is turned off leaving expression of c-met, myogenin and MRF4 (Cornelison & Wold, 1997). Thus, whereas quiescent satellite cells may be determined by c-met expression, activation and differentiation of satellite cells may be determined by the expression of c-met, myf5, MyoD, myogenin, and mrf4.

The single cell RT-PCR technique of Cornelison and Wold allows determination of expression of all the above genes at one time and may be used to identify satellite cells and determine their activation state when incubated in the hypoxic conditions of the present invention. The inventors showed, in particular, that expression of mrf group muscle transcriptional factors is accelerated when skeletal muscle fibers are cultured under 1% oxygen levels. For example, myogenin and mrf4 are not detected in satellites when cultured under normal laboratory oxygen (21%) conditions for 24 hours. However, some satellites cultured with 1% oxygen express mrf4 and some express myogenin after just 24 hours of culture. In addition, a greater percentage of satellites cultured under 1% oxygen conditions express MyoD at 24 hours when compared to the normal culture conditions. This is an example of changes in the timing of differentiation genetic pathways as a consequence of low oxygen culturing conditions.

Differentiated skeletal muscle has a distinctive appearance: myotubes are large fused cells with multiple nuclei aligned coordinately. The myofiber has distinctive, patterned striations. These features are used to define the appearance of newly regenerated muscle from satellites in culture. In addition, specific proteins, such as myosin heavy chain, are expressed by the differentiated fused myotube and are detected using antibody staining.

The methods of this present invention may be utilized to produce both slow- and fast-twitch myofibers (Cornelison & Wold, 1997). Regardless of muscle fiber type, in another embodiment, the muscle produced by the methods of the present invention are used to produce muscle satellites and/or fibers for the purpose of clinical transplantation. In theory satellites and or their progeny could be transplanted to treat muscular diseases such as the muscular dystrophies, or atrophy due to trauma, nerve damage, or disuse. For muscular dystrophies, the satellites and progeny would provide missing gene product (dystrophin, for example) necessary for normal muscle strength. In other cases, missing normal muscle mass would be regenerated from transplanted satellites and progeny. Satellite cells activated under hypoxic conditions may be transplanted into a patient without further differentiation. This protocol may be particularly useful in patients who lack functional satellites to activate because they lack muscle mass. The protocol may also be useful in patients who have satellites that do not regenerate normal muscle (muscular dystrophies), if the donor cells express corrective gene product.

Central Nervous System Cells

The hypoxic culturing conditions of the present invention may also be used in methods comprising cells of the nervous system. Neural stem cells and stem cell progeny (daughter stem cells and progenitor cells) proliferate and differentiate. Undifferentiated neural progenitor cells differentiate into neuroblasts and glioblasts which give rise to neurons and glial cells. During development, cells that are derived from the neural tube give rise to neurons and glia of the CNS. Certain factors present during development, such as nerve growth factor (NGF), promote the growth of neural cells.

Methods of isolating and culturing neural stem cells and progenitor cells are well known to those of skill in the art (Hazel and Muller, 1997; U.S. Pat. No. 5,750,376).

Hazel and Muller describe methods of isolating, culturing, and differentiating rat brain neuroepithelial stem cells from both fetal and adult rat brains. Briefly, neural precursors are removed from desired regions of the fetal rat central nervous system by dissection, dissociated to a single-cell suspension, and plated on tissue culture dishes in medium containing the mitogen basic fibroblast growth factor (bFGF). Initially, many of the differentiated neurons die. Proliferating cells are then harvested in a buffered solution. The passaged cells are relatively homogenous for multipotent precursors. To induce differentiation to neurons and glia, the media containing bFGF is removed and replaced with media lacking bFGF.

Subatmospheric culturing conditions can be used in such a protocol from the start of stem cell isolation, in order to enrich the stem cell pool and enhance differentiation into a greater number of cells. Subatmospheric/physiologic culture conditions can also be used after initial plating and division, to up-regulate certain gene products in the more differentiated brain cells. Subatmospheric/physiologic culture conditions can also be used throughout the process to enhance the function of the entire population for transplantation.

Detection of neural stem cell derivatives can be determined by antibody staining. For example, central nervous system multipotential stems are marked by high level expression of the intermediate filament, nestin (Hazel & Muller, 1997). The differentiated neurons are marked by the antibody TUJI (O'Rourke et al., 1997), oligodendrocytes by GaiC (Bosio et al., 1996), and astrocytes by GFAP antibodies (Rutka et al., 1997).

The methods of the present invention may be used to produce neural cells containing a heterologous gene. Methods of producing cells of neural origin comprising a heterologous gene and uses of such cells are described in U.S. Pat. No. 5,750,376 (incorporated herein by reference).

The hypoxic culturing conditions of the present invention may also be used in transplantation protocols for cells of the central nervous system or cells of the peripheral nervous system.

Skin Cells

In another embodiment, the hypoxic culturing methods of the present invention may be used in the culturing of keratinocytes (progenitor cells for skin). Methods of isolating, culturing, and differentiating keratinocytes are well known to those of skill in the art (Jones et al., 1995; Di Cunto et al., 1998). Although keratin 19 is widely considered to be the best available overall marker for keratinocytes (Michel et al., 1996), in preferred embodiments the progenitor cells are distinguished by morphologic criteria because a reliable antibody is not available. Hypoxic/physiologic oxygen conditions can be used from the time of isolation of both fetal and post-natal keratinocytes, in order to facilitate isolation, expansion, and differentiation of these cells.

The skin cells produced by the methods of the present invention are used to produce skin progenitors or tissue for the purpose of clinical transplantation. Transplantation may be used to treat skin injuries such as delayed wound healing, thermal or chemical burns, or severe allergic reactions, or after massive resection of skin for malignancy.

Embryonic Stem Cells

Embryonic stem cells have been used widely in the generation of experimental gene knockout mice. The isolation of embryonic stem cells from human tissue has also been reported (Thomson, 1998). However, as disclosed herein, oxygen concentration has a significant effect on proliferation and differentiation of developmentally primitive cells. Therefore, variation of ambient oxygen in the culture conditions for embryonic stem cells may be an important parameter in the development of specific tissue from these lines for therapeutic purposes. Methods of varying oxygen concentration and assaying for the effect of physiologic/subatmospheric oxygen culture conditions are disclosed herein.

EXAMPLES

A. Method for obtaining a population of mammalian muscle cells

To create single muscle fiber cultures, 100–200 day old female B6D2F1 mice are euthanized (with $CO_2$). The back legs are skinned, amputated at the hip, and the feet removed. The legs are placed into DMEM without phenol red or sodium pyruvate, containing high glucose, L-glutamine, 25 mM Hepes buffer, with pyridoxine hydrochloride (this is a commercial preparation from GibcoBRL, catalog no. 21063-029) at room temperature. The leg muscles are dissected out individually using a dissecting microscope, and teased into small pieces, then placed into 400 U/ml collagenase type I (Worthington Biochemical) in the DMEM formulation above, at 34° C. for 45 min. After digestion, the muscle is placed into a 10-cm plastic dish, and individual live fibers are picked using a protein-coated Pasteur pipet (with a hand-polished tip) into the following medium: DMEM with phenol red+5% chick embryo extract+10% horse serum+antibiotics/antimycotics+L-glutamine+25 mM Hepes, prewarmed to 34° C. incubator with 5% $CO_2$ for 15–30 min. The procedure is repeated with a finer polished tip Pasteur pipet, placing picked fibers into the same Hepes-buffered DMEM medium. A third pick of fibers is performed, this time placing the fibers into DMEM with phenol red+5% chick embryo extract+10% horse serum+antibiotic/antimyocotic+L-glutamine, but without added Hepes (growth medium). Then the fibers are placed either in traditional incubators as above, or in a hypoxia chamber (Billups-Rothenberg, San Diego Calif.) flushed with the appropriate gas mixture which is then placed in the incubator. Hypoxic cultures are maintained in the chamber except during feeding, and feeding time is minimized as much as possible. The chambers are flushed daily.

The above protocol differs from that previously described (Cornelison & Wold, 1997). Significantly, (1) the fibers are dissected in a buffered medium solution rather than in PBS, (2) the temperature at which the collagenase digestion is performed was reduced, (3) Hepes buffered medium is used while the fibers are out of the incubator and cannot be buffered by $CO_2$.

B. Method for enriching progenitor cells in a population

After isolation of single skeletal muscle fibers for culture, half the fibers from one mouse are placed into a 10-cm plastic tissue culture plate containing fiber growth medium, and put into a sealed chamber flushed with 1% oxygen, 5% carbon dioxide and 94% nitrogen. The chamber, containing an open Petri dish with sterile water, is placed into an incubator maintained at 37° C. The remaining half of the fibers (for comparison purposes) are placed in the same incubator, which has carbon dioxide maintained at 5% in room air. After 12 hours, the fibers are placed in fresh, pre-warmed growth medium under a dissecting microscope, then returned immediately to their previous culture conditions. An aliquot of fibers is removed periodically for analysis. Except during necessary cell manipulations, 1% oxygen is maintained in the low-oxygen cultures at all times.

C. Method for differentiating a progenitor cell

After 4–7 days in culture as above, the fibers are placed into pre-warmed medium of DMEM+2% horse serum+penicillin/streptomycin/antimycotic+L-glutamine, then returned to the hypoxia chamber (or control cells to normal culture conditions). The medium is changed one time per week. After several days, differentiating myotubes appear both on the live and dead floating muscle fibers and attached to the bottom of the tissue culture plate. From both locations they can be picked singly using a patch clamp apparatus for analysis of messenger RNA expression patterns, or stained for specific protein products.

REFERENCES

Assy & Minuk, "Liver regeneration: methods for monitoring and their applications," *J. Hepatology*, 26:945–952, 1997.

Barinaga M, "Looking to development's future," *Science* 266:561–564, 1994.

Berthelot & Terqui, "Effects of oxygen, CO2/pH and medium on the in vitro development of individually cultured porcine one- and two-cell embryos," *Reproduction, Nutrition, Development* 36: 241–251, 1996.

Bosio et al., "Functional breakdown of the lipid bilayer of the myelin membrane in central and peripheral nervous system by disrupted galactocerebroside synthesis," *Proc. Natl. Acad. Sci. U.S.A.* 93:13280–13285, 1996.

Cornelison & Wold, "Single-Cell analysis of Regulatory Gene Expression in Quiescent and Activated Mouse Skeletal Muscle Satellite Cells," *Developmental Biology*, 191:270–283, 1997.

Di Cunto et al., "Inhibitory Function of $p21^{Cip1/WAF1}$ in Differentiation of Primary Mouse Keratinocytes Independent of Cell Cycle Control," *Science*, 280:1069–1072, 1998.

Giles & Foote, "Effects of gas atmosphere, platelet-derived growth factor and leukemia inhibitory factor on cell numbers of rabbit embryos cultured in a protein free medium," *Reproduction, Nutrition, Development* 37:97–104, 1997.

Guyton & Hall, eds., "Transport of Oxygen and Carbon Dioxide in the Blood and Body Fluids." In Textbook of Medical Physiology, W. B. Saunders, Philadelphia, 1996, pp. 513–523.

Hazel & Muller, "Culture of Neuroepithelial Stem Cells," *Current Protocols in Neuroscience*, 3.1.1–3.1.6, 1997.

Iyer et al., "Cellular And Developmental Control Of O2 Homeostasis By Hypoxia-Inducible Factor 1 Alpha," *Genes And Development* 12:149–162, 1998.

Jones et al., "Stem Cell Patterning and Fate in Human Epidermis," *Cell*, 80:83–93, 1995.

Kang et al., *Proc. Natl. Acad. Sci. U.S.A.*, 95(23): 13788–13793, 1998.

Kocher et al., *Clin. Cancer Res.*, 1(10):1209–1215, 1995.

Matsuda et al., "Proliferation and differentiation of human osteoblastic cells associated with differential activation of MAP kinases in response to epidermal growth factor, hypoxia, and mechanical stress in vitro," *Biochem. Biophys. Res. Comm.* 249:350–354, 1998.

Michel et al., "Keratin 19 as a biochemical marker of skin stem cells in vivo and in vitro: keratin 19 expressing cells are differentially localized in function of anatomic sites, and their number varies with donor age and culture stage," *J. Cell Science* 109: 1017–1028, 1996.

Nabel et al., *Nature* 362:844, 1993.

Neelakanta & Csete, "Efforts to overcome the liver donor shortage," *Chirurgia Internat.*, 1996.

O'Rourke et al., "Postmitotic neurons migrate tangentially in the cortical ventricular zone," *Development* 124:997–1005, 1997.

Ramsey et al., "Characterization Of The Active Site Iron In Tyrosine Hydroxylase. Redox States Of The Iron," *J. Biol. Chem.* 271: 24395–24400, 1996.

Rutka et al., "Role of glial filaments in cells and tumors of glial origin: a review," *J. Neurosurgery* 87:420–30, 1997.

Papadopoulos et al, "Over-expression of HSP-70 protects astrocytes from combined oxygen-glucose deprivation," *Neuroreport* 7:429–32, 1996.

Storch TG, "Oxygen concentration regulates 5-azacytidine-induced myogenesis in C3H/10T1/2 cultures," *Biochim. Biophys. Acta* 1055:126–129, 1996.

Taylor & Jones, "Multiple new phenotypes induced in 10T1/2 and 3T3 cells treated with 5-azacytidine," *Cell* 17:771–779, 1979.

Thomson et al., "Embryonic Stem Cell Lines Derived from Human Blastocysts," *Science*, 282(5391):1145, 1998.

Yanez & porter, *Gene Ther.*, 592:149–159, 1998.

What is claimed is:

1. A method of accelerating differentiation of a stem cell or a progenitor cell, comprising culturing a starting cell that is a skeletal muscle stem or skeletal muscle progenitor cell in less than 12% oxygen conditions for a time sufficient to produce a skeletal muscle cell that is more differentiated than the starting cell.

2. A method of enhancing production of skeletal muscle cells that are more differentiated than are starting stem cells or progenitor cells, comprising
   a) first culturing skeletal muscle stem cell or skeletal muscle progenitor cell population in less than 12% oxygen conditions to expand the skeletal muscle stem or skeletal muscle progenitor cell population, and
   b) then culturing the expanded population in less than 12% oxygen conditions to further differentiation.

3. A method of manipulating a differentiation pathway of a stem or progenitor cell, comprising the step of:
  a) culturing a stem cell or a progenitor cell population comprising skeletal muscle and non-skeletal muscle cells in less than 12% oxygen conditions to obtain differentiated progeny, such that the percentage of differentiated skeletal muscle cells produced is increased relative to the percentage of non-skeletal muscle cells; and
  b) optionally culturing the differentiated progeny in less than 12% oxygen conditions, such that the differentiated progeny of step a) are further differentiated.

4. The method of claim 1, 2, or 3, wherein the stem cell or progenitor cell is derived from skeletal muscle.

5. The method of claim 1, 2, or 3, further comprising the step of transfecting the stem cell or progenitor cell with a nucleic acid.

6. The method of claim 5, wherein the nucleic acid comprises an expression vector comprising a nucleic acid operably linked to a promoter.

7. The method of claim 1, wherein the stem or progenitor cell is cultured in less than 5% oxygen conditions for a time sufficient to produce a skeletal muscle cell that is more differentiated than the starting cell.

8. The method of claim 7, wherein the stem or progenitor cell is cultured in about 1% to less than 5% oxygen conditions for a time sufficient to produce a skeletal muscle cell that is more differentiated than the starting cell.

9. The method of claim 7, wherein the stem or progenitor cell is cultured in less than 1% oxygen conditions for a time sufficient to produce a skeletal muscle cell that is more differentiated than the starting cell.

10. The method of claim 2 comprising first culturing in less than 5% oxygen conditions to expand the skeletal muscle stem or progenitor cell population.

11. The method of claim 10 comprising first culturing in about 1% to less than 5% oxygen conditions to expand the skeletal muscle stem or progenitor cell population.

12. The method of claim 10 comprising first culturing in less than 1% oxygen conditions to expand the skeletal muscle stem or progenitor cell population.

13. The method of claim 2 comprising culturing the expanded population in less than 5% oxygen conditions to further differentiation.

14. The method of claim 3 comprising culturing the stem cell or progenitor cell population in less than 5% oxygen conditions to obtain differentiated progeny, such that the percentage of differentiated skeletal muscle cells produced is increased relative to the percentage of non-skeletal muscle cells.

15. The method of claim 14 comprising culturing the stem cell or progenitor cell population in about 1% to less than 5% oxygen conditions to obtain differentiated progeny, such that the percentage of differentiated skeletal muscle cells produced is increased relative to the percentage of non-skeletal muscle cells.

16. The method of claim 14 comprising culturing the stem cell or progenitor cell in less than 1% oxygen conditions to obtain differentiated progeny, such that the percentage of differentiated skeletal muscle cells produced is increased relative to the percentage of non-skeletal muscle cells.

* * * * *